(12) United States Patent
Beyer et al.

(10) Patent No.: US 10,188,493 B2
(45) Date of Patent: Jan. 29, 2019

(54) SURGICAL MESH WITH DIMENSIONALLY STABILIZED PORE

(75) Inventors: Sarah Beyer, Pinebluff, NC (US); Mark Jessup, Aberdeen, NC (US)

(73) Assignee: Atex Technologies, Inc., Pinebluff, NC (US)

( * ) Notice: Subject to any disclaimer, the term of this patent is extended or adjusted under 35 U.S.C. 154(b) by 1372 days.

(21) Appl. No.: 14/117,072

(22) PCT Filed: May 14, 2012

(86) PCT No.: PCT/US2012/037718
§ 371 (c)(1),
(2), (4) Date: Apr. 9, 2015

(87) PCT Pub. No.: WO2012/158590
PCT Pub. Date: Nov. 22, 2012

(65) Prior Publication Data
US 2015/0216648 A1      Aug. 6, 2015

Related U.S. Application Data

(60) Provisional application No. 61/485,699, filed on May 13, 2011.

(51) Int. Cl.
*D04B 1/22*    (2006.01)
*D06C 3/10*    (2006.01)
*A61F 2/00*    (2006.01)

(52) U.S. Cl.
CPC .............. *A61F 2/0063* (2013.01); *D04B 1/22* (2013.01); *A61F 2002/0068* (2013.01); *D06C 3/10* (2013.01)

(58) Field of Classification Search
CPC ............................. D06F 37/261; D06F 37/262
See application file for complete search history.

(56) References Cited

U.S. PATENT DOCUMENTS

| | | | |
|---|---|---|---|
| 5,569,273 A | 10/1996 | Titone et al. | |
| 6,287,316 B1 * | 9/2001 | Agarwal | A61F 2/0063 606/151 |
| 2002/0116070 A1 * | 8/2002 | Amara et al. | |
| 2009/0036996 A1 | 2/2009 | Roeber | |
| 2012/0016388 A1 | 1/2012 | Houard et al. | |

FOREIGN PATENT DOCUMENTS

| | | |
|---|---|---|
| EP | 1060714 A2 | 12/2000 |
| WO | 20081075398 A2 | 6/2008 |
| WO | 2010/086515 A1 | 5/2010 |

* cited by examiner

*Primary Examiner* — Jenna L Johnson
(74) *Attorney, Agent, or Firm* — Hoffmann & Baron, LLP

(57) ABSTRACT

A system, method and fabric having a dimensionally stabilized pore. The system has a mesh fabric having a pore, such pore having a first pore perimeter. The system has a support having a support outer perimeter. The support is received into the pore so that the pore perimeter is in contact with the outer support perimeter. When the fabric is thermoset, the pore permanently assumes the shape of the outer support perimeter.

18 Claims, 9 Drawing Sheets

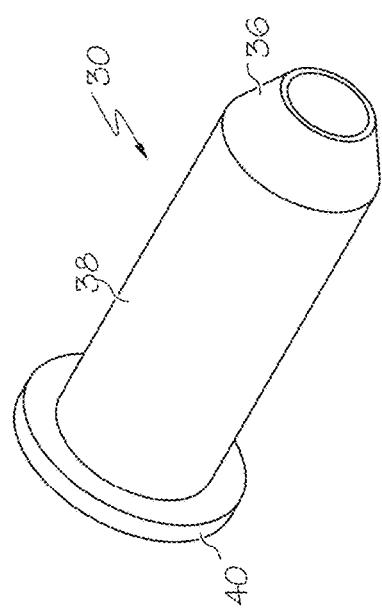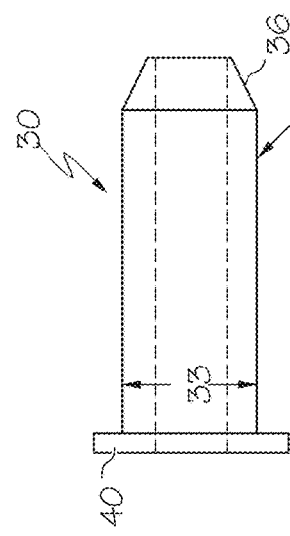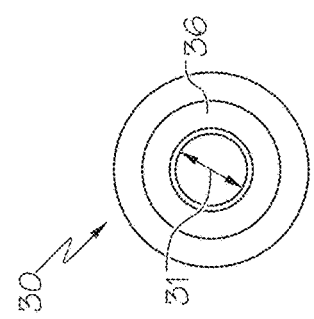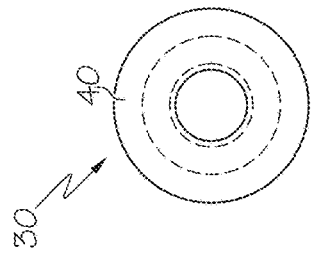

SURGICAL MESH WITH DIMENSIONALLY STABILIZED PORE

CROSS REFERENCE TO RELATED APPLICATIONS

This application is the National Stage of International Application No. PCT/US2012/037718, filed May 14, 2012, which claims the benefit of U.S. Provisional Patent Application No. 61/485,699, filed May 13, 2011, which is incorporated herein by reference in its entirely.

FIELD OF THE INVENTION

The embodiments herein are directed to a system and fabric having at least one dimensionally stabilized pore and a method of making the same.

BRIEF DESCRIPTION OF THE DRAWINGS

FIG. 6A is perspective view of the taper of the system of FIG. 2.

FIG. 6B is a rear view of the taper of the system of FIG. 2.

FIG. 6C is a side view of the taper of the system of FIG. 2.

FIG. 6D is a front view of the taper of the system of FIG. 2.

DETAILED DESCRIPTION OF THE INVENTION

Figure 1:
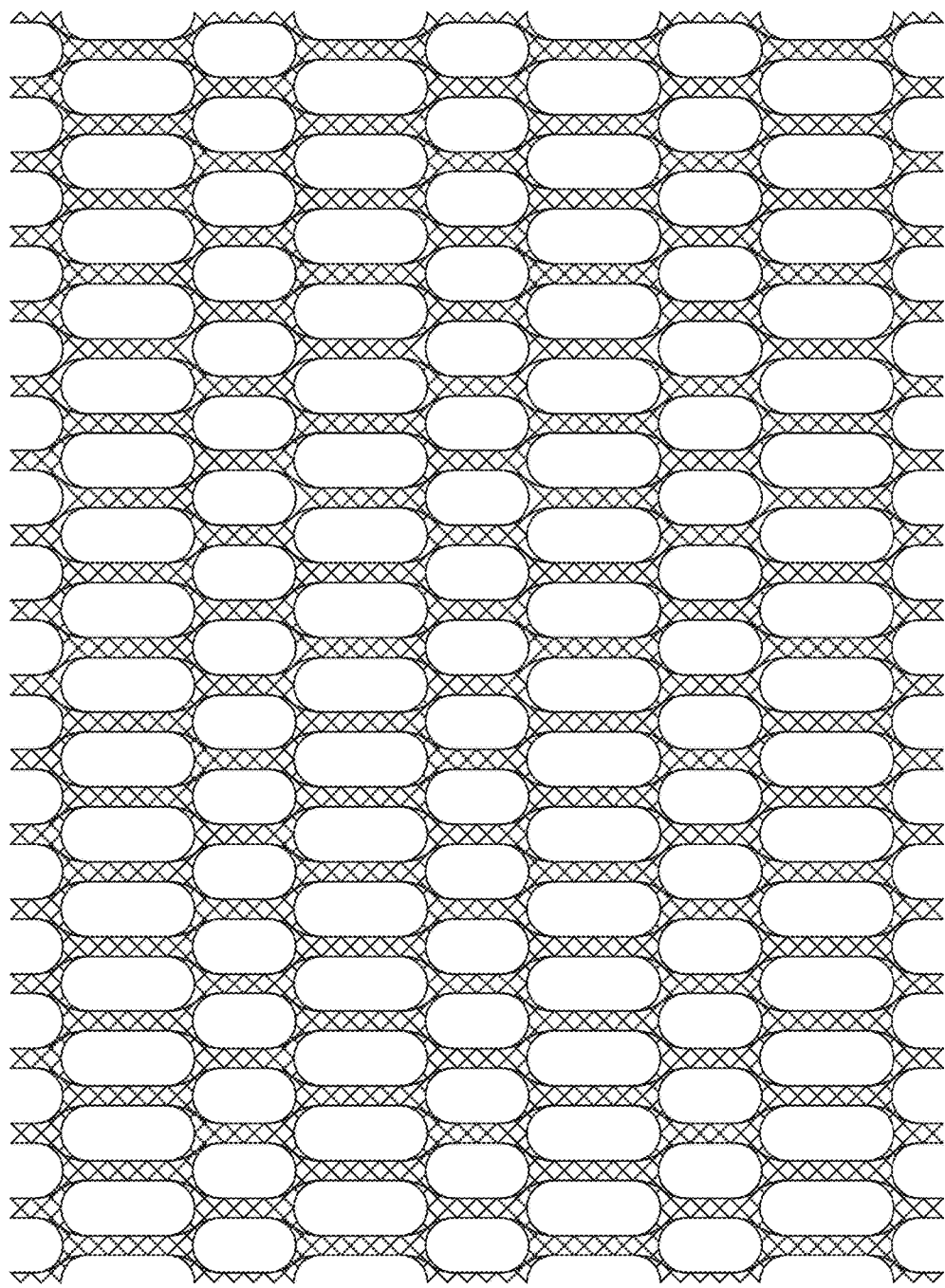
FIG. 1 is a front view of surgical mesh fabric.

Surgical mesh fabric has a number of different uses. In particular, surgical mesh fabric may be used in a variety of procedures including reinforcement of the pelvic floor or the abdominal wall. Surgical knit mesh can be manufactured in a variety of different ways so as to create a final product that has different size pores and different tensile strengths and flexibility characteristics to suit the particular application. Where surgical mesh is used in the reinforcement of pelvic floor or abdominal wall procedures, it is desirable to make the pore size as large as possible so as to encourage cell in-growth. However, if pore size becomes too large, tensile strength may be compromised. Thus, for an effective material for use in the reinforcement procedure for a pelvic floor or an abdominal wall, the pore size becomes a compromise between maintaining the necessary tensile strength in the material and the desire to achieve an open structure to encourage cell in-growth.

In some applications, it is desirable to incorporate surgical mesh as a part of a medical device. As such, there may be a need to join or affix the mesh with other parts or layers of the medical device. Often times the mesh is joined to a device or part by fixing the mesh to the device with a rivet or other joining means. When a rivet is used, the mesh must have a sufficiently large opening to receive the rivet. It would be a simple manufacturing step to cut or punch the appropriate sized hole into the mesh to accommodate any attachment of the mesh to a rivet or other joining mechanism. However, the tensile strength of the mesh is diminished when the fibers forming the mesh are cut. In addition, the cut fibers may act as an irritant when used as part of an implantable device. Furthermore, the cut ends add a risk that a free end or fiber may dislodge or loosen and become separated from the device causing further complications to the patient. Thus, it is desired to form the needed hole in the fabric by a means other than cutting to maintain the strength of the mesh and thus the overall performance of the assembly.

The preferred mesh fabric of the embodiments described herein incorporates a way of forming a pore in the mesh fabric without compromising the integrity of the mesh. In particular, the system, method and fabric of the preferred embodiments described herein create a dimensionally stabilized pore which is a preferred advantage in manufacture. The term "dimensionally stabilized" is used to refer to a targeted pore within a fabric that is permanently shaped during an annealing process. The preferred embodiments, and method and system for making the same are described in detail below.

In one embodiment, a system for forming a stabilized pore within a mesh fabric may include a support having a support outer perimeter. For use with a mesh fabric having at least one pore having a pore perimeter, the support is capable of being received into the pore of the mesh fabric so that the pore perimeter of the mesh fabric is in contact with the outer support perimeter. When the fabric is heat set for a predetermined time at a predetermined temperature, the first pore assumes the dimension of the outer support perimeter.

A first preferred embodiment 10 includes a surgical mesh knit fabric 14 made using a 14 gauge knitting machine. The yarn comprising the mesh knit fabric 14 is 3 mil (0.003 inch) diameter polypropylene. However, it is anticipated that any thermoplastic polymer may be used in this application. The selection of a particular thermoplastic polymer would depend on the qualities of the product desired. In the case at hand, the first embodiment is a mesh knit fabric 14 having a knit pattern is as follows:

a first bar pattern chain of 1/0-2/3-2/1-2/3-2/1-2/3-(1/0-1/2)×3;
a second bar pattern chain of 2/3-1/0-1/2-1/0-1/2-1/0-(2/3-2/1)×3; and
a third bar pattern chain of 0/0-1/1.

There are 26 courses per inch. The resulting warp knit fabric 14 produces a series of pores or holes within the knit fabric. Targeted pores 12 are those pores that will be the target of the system and method of the present invention which will be described in more detail below. A representative sample of the mesh knit fabric 14 described above is shown in FIG. 1. It should be noted that prior to heat setting, the mesh knit fabric 14 is made in rows of hexagonal pores or openings. In the sample of FIG. 1, there are alternating rows of larger hexagonal pores and smaller hexagonal pores. In the row of larger hexagonal pores, the pores typically measure less than about 2 mm wide and about 7 mm long.

Figure 2:
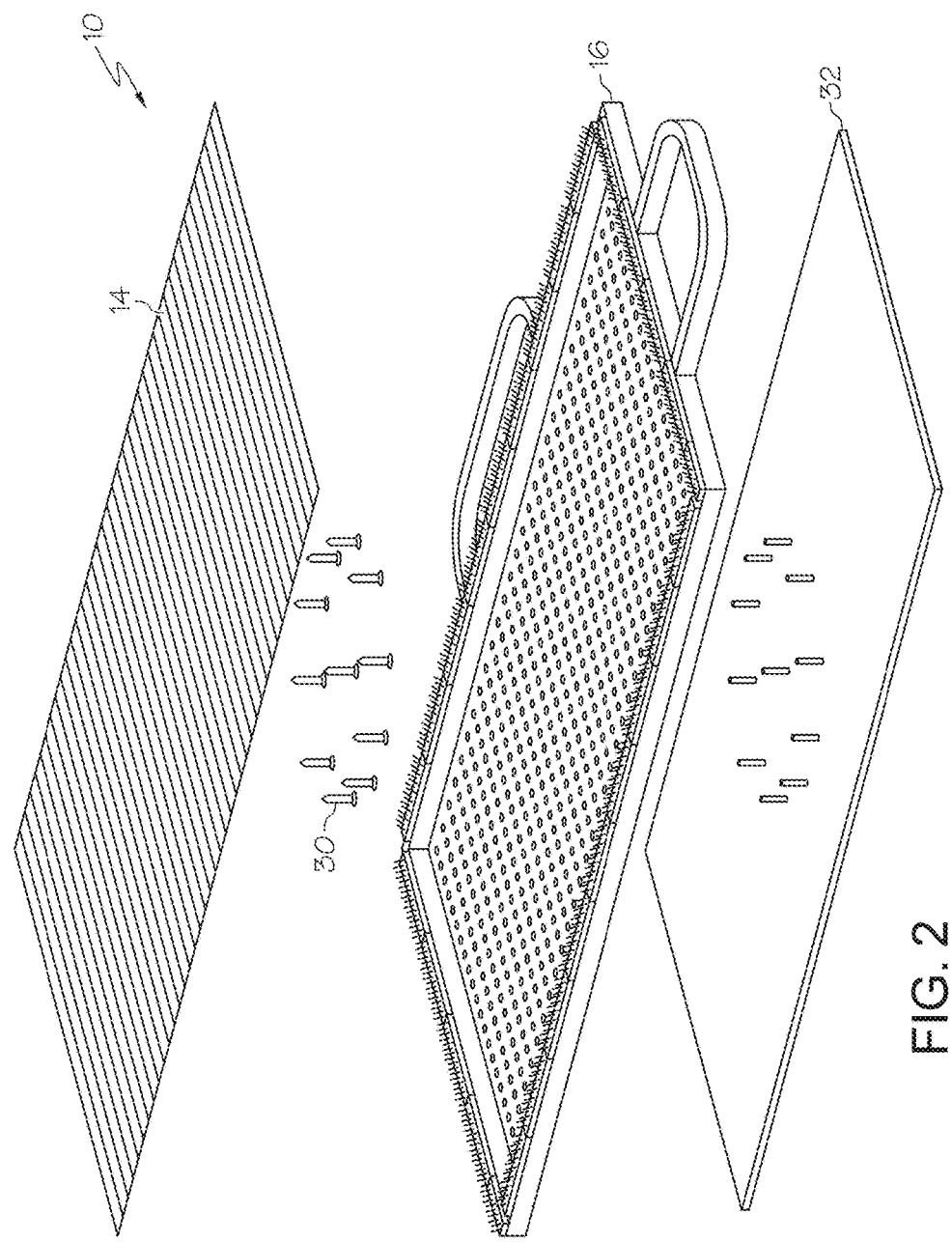
FIG. 2 is a perspective exploded view of the system of the first embodiment.
Figure 3C:
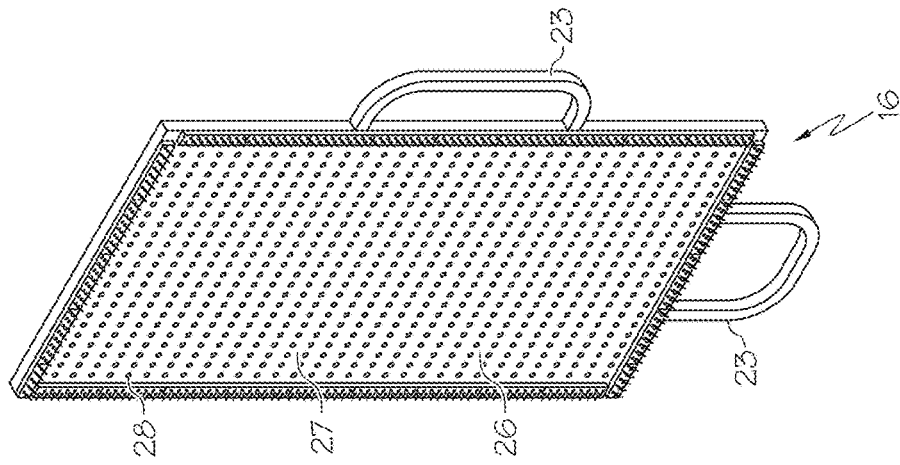
FIG. 3C is a perspective view of the pin frame assembly of the first embodiment.
Figure 3B:
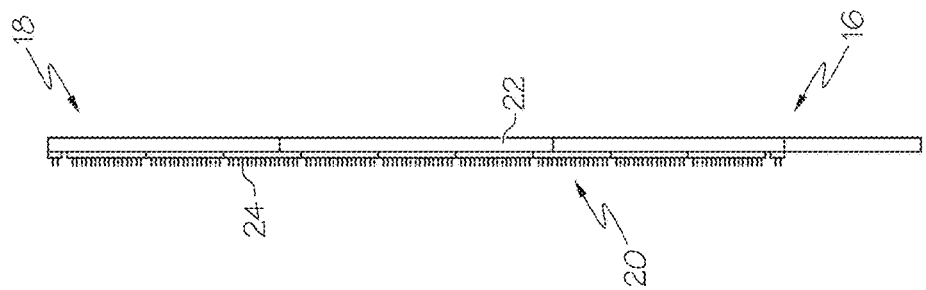
FIG. 3B is a side view of the pin frame assembly of the first embodiment.
Figure 3A:
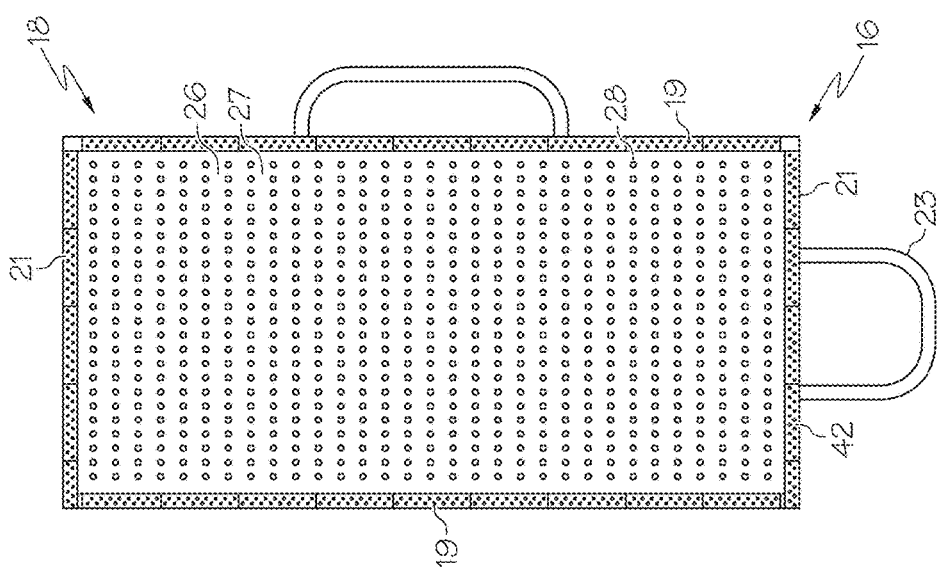
FIG. 3A is a front view of the pin frame assembly of the first embodiment.
Figure 4A:
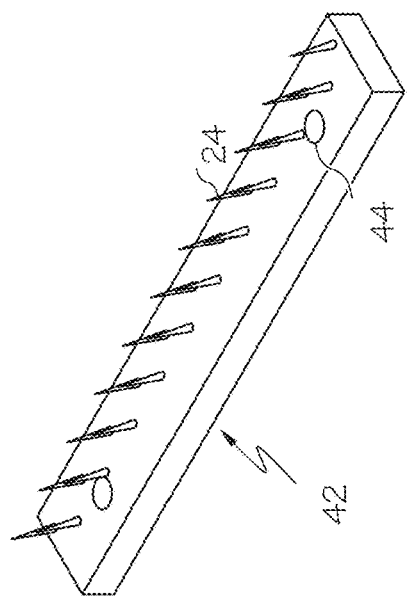
FIG. 4A is a perspective view of a pin section of the pin frame assembly of FIGS. 3A-3C.
Figure 4D:
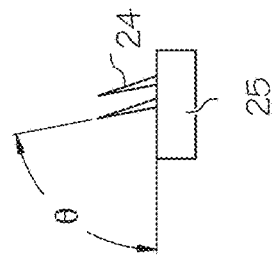
FIG. 4D is a side of a pin section of the pin frame assembly of FIGS. 3A-3C.
Figure 4B:
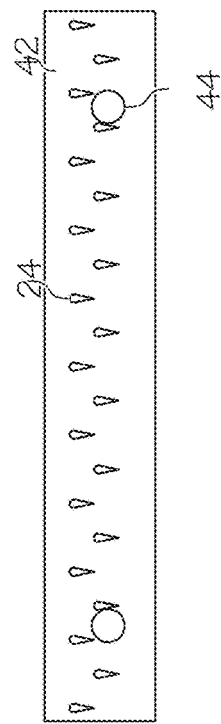
FIG. 4B is a top view of a pin section of the pin frame assembly of FIGS. 3A-3C.
Figure 4C:
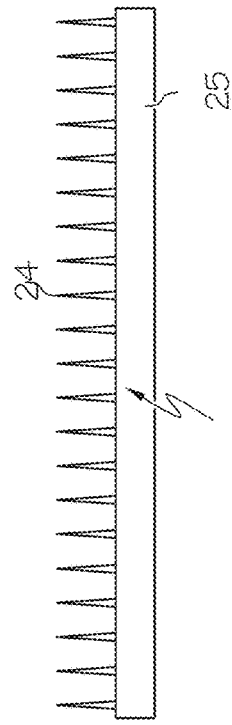
FIG. 4C is a front view of a pin section of the pin frame assembly of FIGS. 3A-3C.

To create the dimensionally stabilized pores of the preferred embodiment 10, a pin frame assembly 16 and peg plate 32 are used, as shown generally in FIG. 2. The pin frame assembly 16 of the first preferred embodiment 10, shown in more detail in FIGS. 3A, 3B and 3C, includes a rectangular frame 18. The rectangular frame 18 includes a pair of parallel vertical sections 19 and a pair of parallel horizontal sections 21. The vertical 19 and horizontal sections 21 form a rectangular shaped frame. The rectangular frame 18 also has an upper surface 20 and a lower surface 22. A plurality of upwardly extending pins 24 are fixed to the upper surface 20 of the frame 18. In preferred embodiment 10, the pins 24 are fixed to a pin section 42, as shown in detail in FIGS. 4A, 4B, 4C and 4D. Each pin section 42 includes section recesses 44. The recesses 44 receive fasteners, such as screws (not shown), to secure the pin sections 42 to the rectangular frame 18. The pins 24 are fixed to the section 42 at an angle θ. It is preferable that θ be 75°. It should be noted that the pin angle θ may range from about 25° off vertical to completely vertical (i.e., θ would be 90°). In use, the pins 24 are fixed to the rectangular frame 18 with the pins angled away from the center of the frame. This arrangement helps to hold the mesh fabric 14 more effectively and minimize any slippage or movement of the fabric, which will be described in more detail below.

In the first preferred embodiment 10, the pin sections 42 have staggered rows of pins 24. Each row includes about 10 or 11 pins per section 42. There are about 9 pin sections along the length of the rectangular frame 18 and about 4.5 along the width. Further, in the preferred embodiment 10, the pins 24 are about 7 mm long and have a diameter of about 1 mm. The ends of the pins are pointed. The sharp pointed end of the pins helps to grab the mesh knit fabric 14. The pin 24 is fixed to the pin section 42.

The pins 24 are designed to engage with the mesh fabric 14 and hold it taut during fabrication, which will be described in more detail below. Returning to FIGS. 3A, 3B and -3C, the pin frame assembly 16 also includes a pair of handles 23. One handle 23 is located adjacent to a vertical section 19 and one located adjacent to a horizontal section 21. The handles 23 provide ease of handling of the pin frame assembly 16 during fabrication, which will be discussed in more detail below. The pin frame assembly 16 of the first preferred embodiment 10 also includes a perforated plate 26 fixed to the lower surface 22 of the frame 18 and extending across the length and width of the frame. The perforated plate 26 has a series of holes 28 extending through the plate. The dimension and position of each hole 28 is designed to align with the peg plate 32 which will be described in more detail below. The perforated plate 26 has an upper perforated plate surface 27 that is joined to the lower surface 22 of the rectangular frame 18.

Figure 5C:
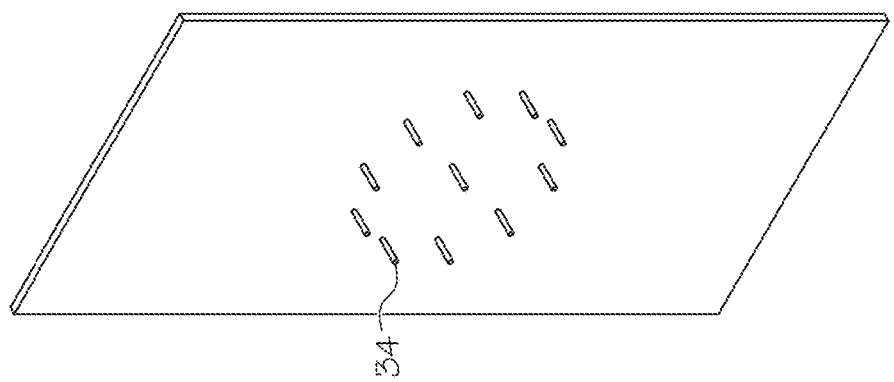
FIG. 5C is a perspective view of the peg plate of the system of FIG. 2.
Figure 5B:
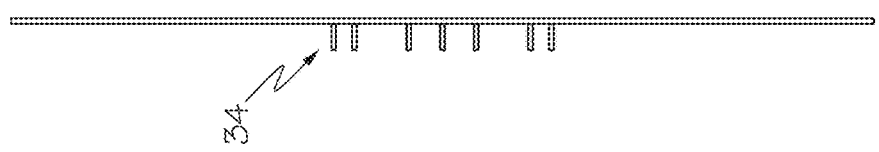
FIG. 5B is a side view of the peg plate of the system of FIG. 2.
Figure 5A:
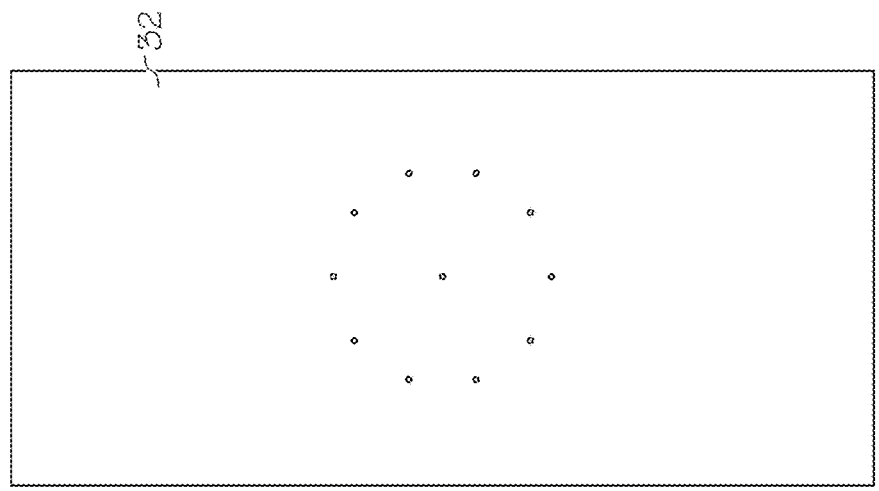
FIG. 5A is a front view of the peg plate of the system of FIG. 2.

FIGS. 5A, 5B and 5C show the peg plate 32 of the first embodiment 10. The peg plate 32 is generally flat and has a similar shape to that of the rectangular frame 18. The peg plate 32 has a series of upwardly projecting pegs 34 extending perpendicular from the plane of the peg plate. The arrangement of the pegs 34 is such that they are received by the holes 28 of the perforated plate 26 when the pin frame assembly 16 is lowered over the peg plate which is described in more detail below. It should be noted that the number and arrangement of pegs 34 may vary as the number and location of targeted pores 12 changes. The pegs 34 may be secured to the peg plate 32 by threaded fasteners (not shown). Thus the peg 34 will be located on the peg plate 32 at a location where a dimensionally stabilized pore is desired. Because the pegs 34 are received into the holes 28 of the perforated plate 26, the outer diameter of the peg cannot exceed the diameter of the hole 28.

In process, the pegs 34 are received into the perforated plate 26 and provide positional support to the tapers 30, shown in detail in FIGS. 6A, 6B, 6C and 6D. In the first preferred embodiment 10, each taper 30 is preferably about 0.778 inches in length. Each taper 30 is hollow having an interior diameter 31 and a maximum outer diameter 33. It is preferred that the interior diameter of the taper 30 is about 0.136 inches, and the maximum outer diameter 33 is preferably about 0.258 inches. The taper 30 has a tapered section 36 and a cylindrical section 38. The tapered section 36 preferably angles from preferably 0.258 inches diameter radially inward to 0.136 inches diameter. The tapered section 36 is preferably about 0.109 inches long. The preferred embodiment taper 30 also has a collar 40. The collar 40 is located at the opposite end of the taper 30 from the tapered section 36. The collar 40 is fixed to the cylindrical section 38 and extends radially outward. In the first preferred embodiment 10, the collar 40 has an outer diameter of about 0.375 inches and a thickness of about 0.039 inches. It is important to note that the outer diameter of the collar should be greater than the diameter of the holes 28 in the perforated plate 26 for reasons set forth in detail below.

To create dimensionally stabilized pores, the pin frame assembly 16 is placed above the peg plate 32 so that the pegs 34 are in alignment with the holes 28 in the perforated plate 26. Once this occurs, the pin frame assembly 16 is lowered over the peg plate 32 and the pegs protrude upward from the perforated plate 26 and into the area surrounded by the rectangular frame 18. The tapers 30 are then placed on the pegs 34 in the locations where dimensionally stabilized pores are desired. Each taper 30 is placed above the peg 34 and the inner diameter 31 of the taper is received by the other diameter of the peg. Next, the mesh knit fabric 14 is arranged on the pin frame assembly 16 so that the fabric is pulled taut across the length and width of the frame 18. This is accomplished by causing one edge of the mesh knit fabric 14 to be received by the plurality of pins 24 on one side of the rectangular frame 18 first, then pulling the fabric to the opposed edge to be received by the pins therein. Then the other remaining pair of edges is received into pins on the corresponding sides of the rectangular frame. Care must be taken to ensure that the fabric 14 is aligned properly so that the targeted pores 12 to be dimensionally stabilized are accurately positioned on the pin frame assembly 16 directly above the tapers 30 previously positioned on the pegs 34.

As the fabric 14 is properly positioned within the pin frame assembly 16, the targeted pore(s) 12 within the fabric located immediately above a taper 30 are forced downwardly over the taper 30 as the fabric is moved onto the pins 24 on the rectangular frame 18. This causes the targeted pore 12 to move from contact with the tapered section 36 of the taper 30 to the cylindrical section 38 of the taper. The diameter of the targeted pore in its knitted state is slightly less than the outer cylindrical diameter 33 of the taper 30. This results in a stretching of the targeted pore 12 and further causes the yarns in the area surrounding the targeted pore to be pulled towards the pore as a result of the stretching. As a result, the targeted pore 12 is in a distended state as it fully receives the cylindrical section 38 of the taper 30 and the surrounding yarn sections have given up some of their width to achieve this state. In other words, the distended pore takes from the adjacent pores some of their width. The process of adjusting the fabric 14 over the tapers 30 continues until each pore to be dimensionally stabilized has a taper 30 fully inserted therein so that the pore 12 receives the cylindrical section 38 of the taper 30.

After all of the tapers 30 are received into the targeted pores 12, the pin frame assembly 16 is lifted by the handles 23 off of the peg plate 32. Because the collar 40 of the taper 30 has an outer diameter that is larger than the diameter of the holes 28 in the perforated plate 26, the tapers 30 remain in position within the fabric 14. The collar 40 of each taper 30 rests on the upper surface 27 of the perforated plate 26. As the mesh fabric 14 shifts slightly with the weight of the engaged collars 40 therein, the collars 40 resting on the upper surface of the perforated plate 26 help to stabilize the fabric 14 so that it does not sag with the weight of the tapers 30.

The pin frame assembly 16 with the tapers 30 within the targeted pores 12 is then placed in an annealing oven. When polypropylene yarn is used in the manufacture of the mesh fabric 14, the preferred annealing temperature is between 290° F. and 310° F., but preferably 304° F., and the anneal time is between 5 to 10 minutes, but preferably 9 minutes for the first preferred embodiment 10.

In general, the annealing temperature of any thermoplastic polymer yarn or fiber is somewhere between the fabrication temperature and the melting temperature of the yarn. A differential scanning calorimeter analysis will indicate the melting point and any other heat set activity of the tested fiber, yarn or the fabric. Where the yarn or fiber has been previously heat set, it is necessary to exceed any previous heat set temperature in order to effectively anneal the fiber or fabric a second time. However, where the fiber or yarn has not been previously heat set, arriving at the most effective annealing temperature is a matter of trial and error. If the anneal temperature is too close to the melting temperature, the mesh fabric may begin to thermally degrade. If the temperature is too close to fabrication temperature, an insufficient level of annealing will occur and the heat set will be ineffective. It should also be noted that the annealing process is a factor of time as well as temperature. Heat accumulation will occur to some extent in any annealing process. The extent of heat accumulation will vary depending on anneal time, temperature and other fabrication factors such as materials used in the process.

Figure 7:
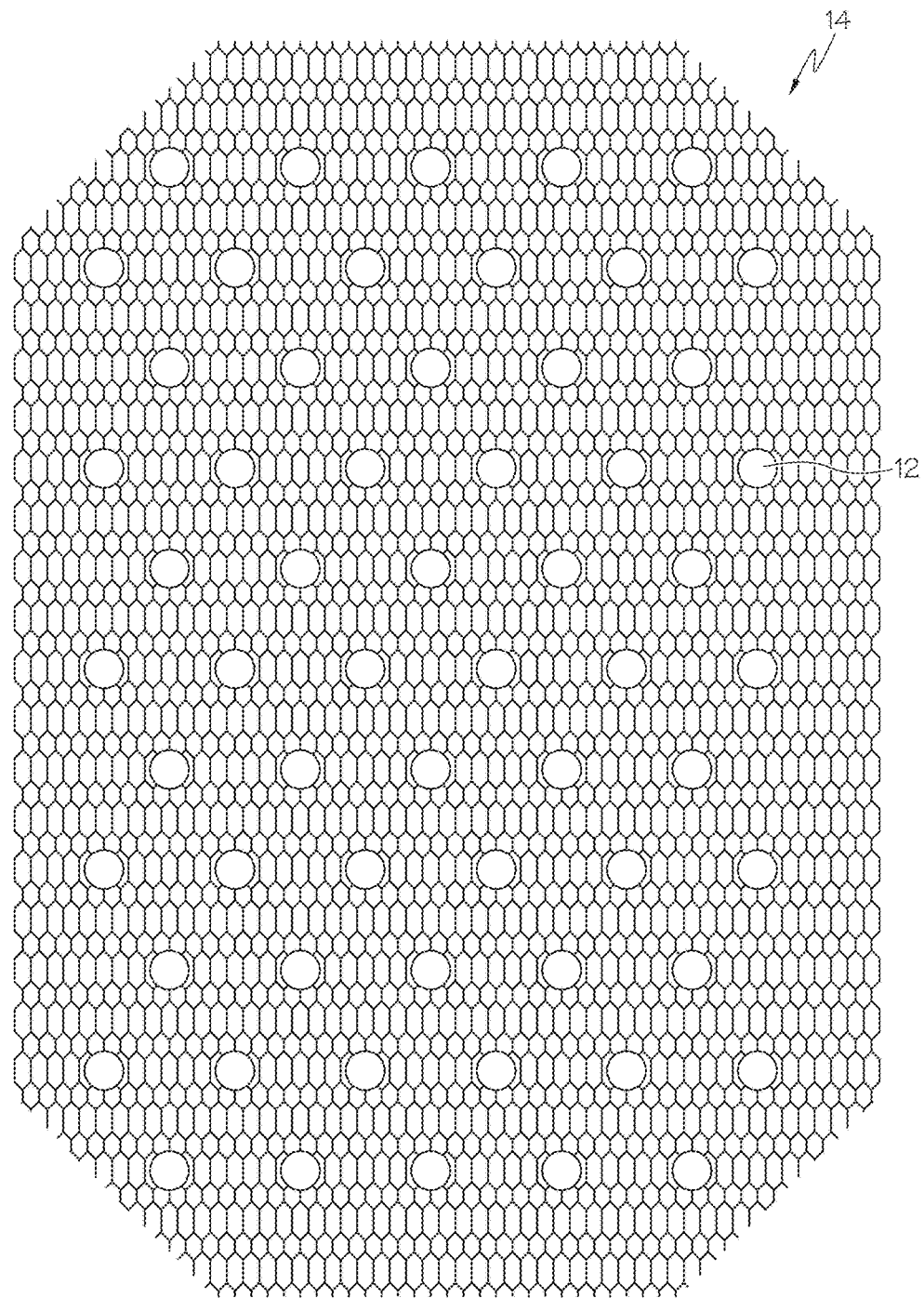
FIG. 7 is a front view of the surgical mesh fabric having dimensionally stabilized pores.
Figure 8:
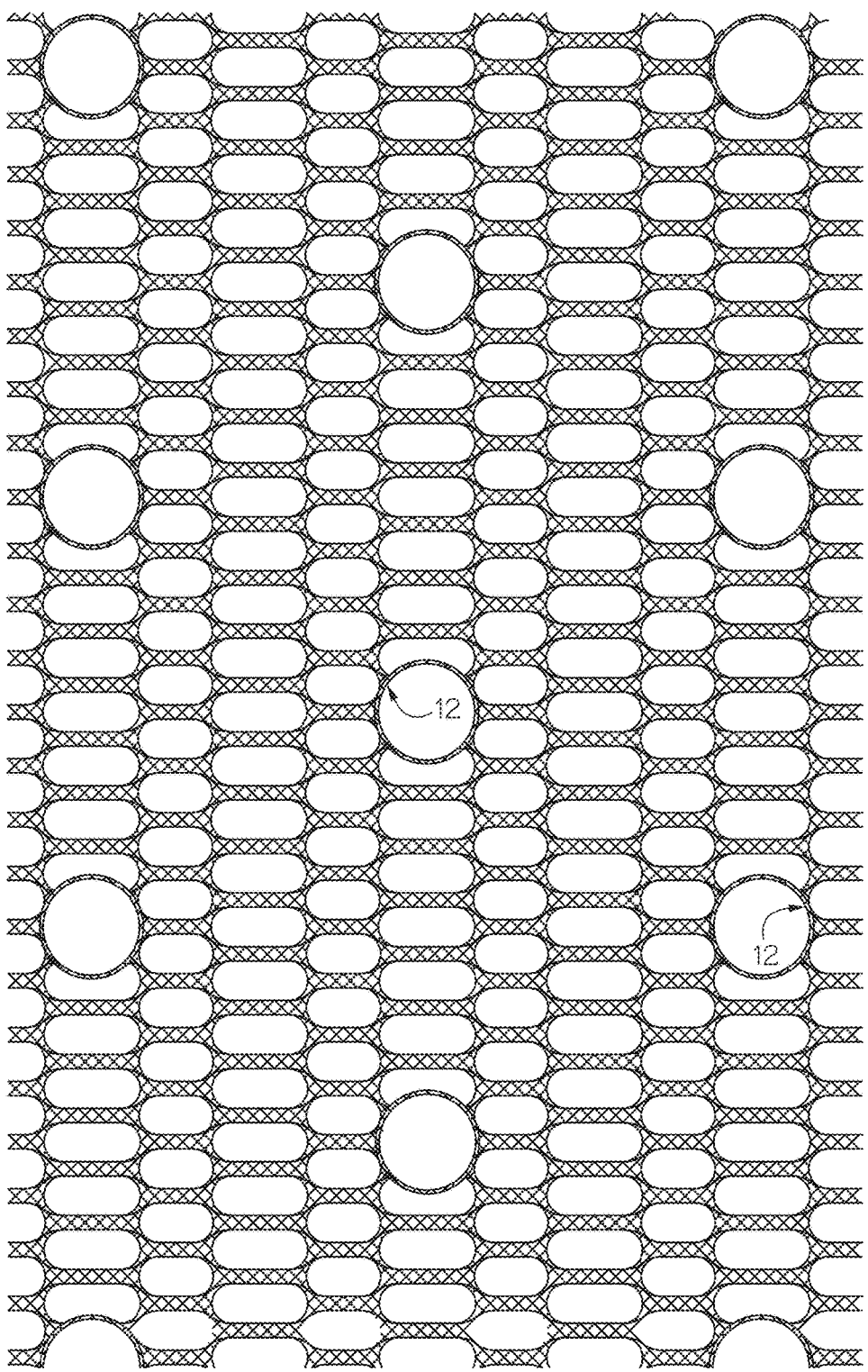
FIG. 8 is an enlarged view of the surgical mesh fabric of FIG. 7.
Figure 9:
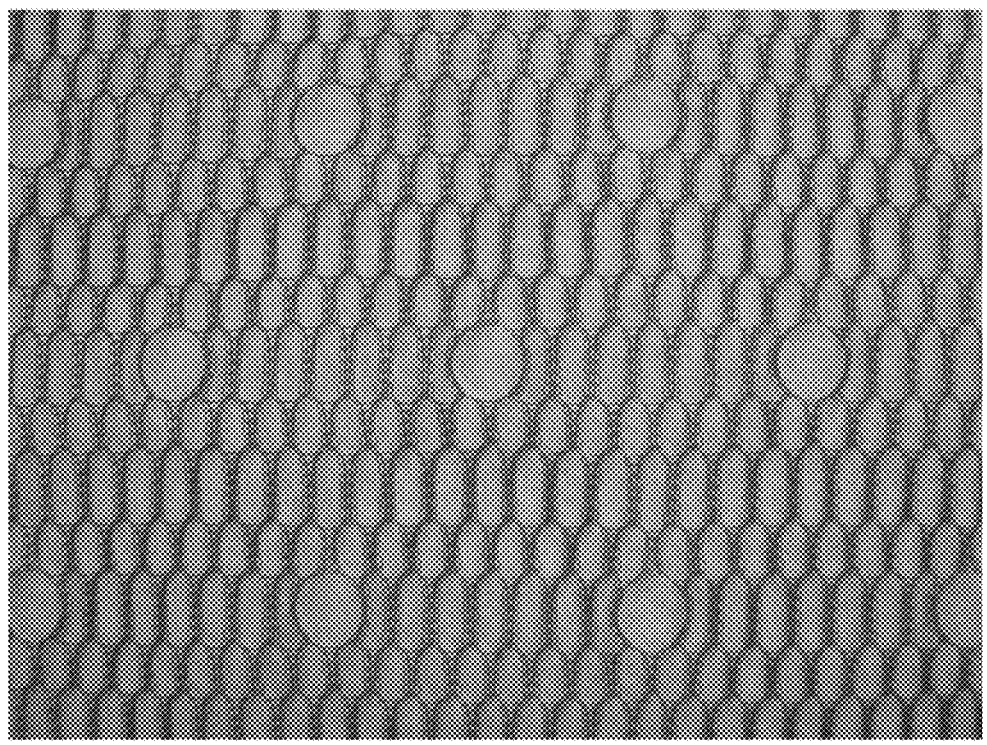
FIG. 9 is a photograph of the surgical mesh fabric having dimensionally stabilized pores, as similarly shown in FIG. 8.

With regard to the fabrication of the first preferred embodiment 10, when the anneal time has elapsed, the pin frame assembly 16 is removed from the oven and allowed to cool. The pin frame assembly 16 is repositioned over the peg plate 32. The pin frame assembly 16 is lowered onto the peg plate 32 so that the tapers 30 are again received into the pegs 34. After sufficient cooling time has elapsed, preferably at least five (5) minutes, the fabric 14 is then disengaged from the pins 24 along the edges of the rectangular frame 18. The cooling also causes the targeted pore 12 to disengage from contact with the cylindrical section 38 of the taper 30. Upon removal of the fabric 14, the targeted pores 12 are permanently enlarged and have permanently assumed the shape of the cylindrical section 38 of the taper 30. The fabric 14 incorporating the dimensionally stabilized pores 12 is now ready for further manufacturing. A drawing of the resulting dimensionally stabilized pore 12 in the surgical mesh fabric is shown in FIG. 7, and in detail in FIG. 8, and also shown in a photograph, which is FIG. 9.

Using the preferred mesh knit fabric described above and after forming stabilized pores therein, a burst strength test was conducted on samples of the preferred embodiment described herein. The burst strength test is described as follows.

The preferred embodiment of the present invention is designed to maintain strength of the fabric while providing pores or holes in the fabric for joining or fastening to other components of a medical device. Applicant has tested the strength of the fabric of the first preferred embodiment 10, in comparison to fabric without any holes or pores (Column A) and with fabric with holes made by cutting (Column C). The results are provided below in Table 1. In column A are mesh samples made using the warp knit fabric described herein, but without the addition of the formation of the pores 12. In column B are mesh samples made in accordance with the detailed description above including the pores 12. In column C are mesh samples made using the warp knit fabric described herein but instead of creating pores 12, the warp knit fabric was cut with holes in the same location as the pores 12 of the warp knit fabric of the first embodiment 10. The test was conducted in accordance with ASTM D 3786-06 and using a Truburst 2 Model 810 Intelligent Bursting Strength Tester. Each test sample was placed so that the center of a cut, dimensionally stabilized or knit pore was centered within the test area. The test area was a 7.3 cm$^2$ circle. As can be seen from the results, the strength of the mesh fabric with the dimensionally stabilized pores is generally greater than fabric with pores cut therein. Further, the mesh fabric with dimensionally stabilized pores showed a strength nearly as high as that of fabric having no pores therein.

TABLE 1

Comparison of Burst Strength (psi)

| Specimen | A<br>Standard Mesh without fabricated Holes | B<br>Mesh Fabricated with Distended Pores | C<br>Mesh fabricated with Cut Holes Equivalent to Distended Pore Size |
|---|---|---|---|
| 1 | 51.66 | 61.73 | 24.98 |
| 2 | 52.09 | 56.09 | 15.34 |
| 3 | 58.66 | 58.55 | 16.7 |
| 4 | 61.77 | 56.95 | 25.48 |
| 5 | 64.02 | 57.55 | 14.59 |
| 6 | 58.55 | 58.45 | 16.52 |
| 7 | 60.3 | 58.05 | 21.77 |
| 8 | 53.23 | 56.59 | 17.09 |
| 9 | 57.41 | 50.77 | 14.77 |
| 10 | 54.63 | 54.8 | 23.41 |
| Average | 57.232 | 56.953 | 19.065 |
| SD | 4.22 | 2.85 | 4.35 |

It should be noted that while this description has focused on circular pore perimeters, it is anticipated that pores of other shapes, such as oval, square, rectangle, and the like, may be dimensionally stabilized in the same manner. It should also be noted that the pore array shown and described in the first preferred embodiment may be changed to suit a different device. Furthermore, the diameter of the tapers and the pore diameter may be altered to accommodate other devices or applications.

It should be further noted that while the discussion above has focused on a knit mesh fabric for use in abdominal tissue repair, other applications of the present invention may be made in the area of woven or braided materials. For example, a woven fabric may be created so as to have one or a plurality of dimensionally stabilized pores in accordance with the present invention. Such dimensionally stabilized pores may be used to provide suture guidance or reinforcement. In addition a dimensionally stabilized pore may be created in accordance with the present invention so as to provide a location for attachment to a medical device or receive a suture or the like.

As used herein, the singular forms "a," "an," and "the" include plural referents unless the context clearly dictates otherwise. Thus, for example, the term "a yarn" or "a pore" is intended to mean a single yarn or a single pore, or more than one yarn or pore. Furthermore, uses within the specification of terms such as "upper," "lower," "vertical," "horizontal," and the like are words of convenience used to describe the structure and function of the parts of the embodiments herein relative to each other and are not meant in any way to be construed as limiting terms.

The invention claimed is:

1. A method of stabilizing a pore within a mesh fabric comprising the steps of:
   providing a mesh knit fabric made of a plurality of thermoplastic polymer yarns, the fabric having a first pore, the first pore having a first perimeter;
   providing a frame comprising pins;
   placing at least a portion of the fabric surrounding the first pore over the pins of the frame, whereby the portion of the fabric is temporarily held taut to define a taut fabric portion;
   providing a support having an outer perimeter comprising a shape and having a tapered section;
   inserting the support into the first pore so that the first pore perimeter is in contact with the outer perimeter of the support; and
   placing the taut fabric portion and the support in an oven for a predetermined time at a predetermined temperature, whereby the first pore perimeter assumes the shape of the outer perimeter of the support.

2. The method of claim 1 wherein the mesh knit fabric is made from 3 mil diameter polypropylene yarn.

3. The method of claim 1 wherein the mesh knit fabric is made using the following knit pattern:
   a first bar pattern chain of 1/0-2/3-2/1-2/3-2/1-2/3-(1/0-1/2)×3;
   a second bar pattern chain of 2/3-1/0-1/2-1/0-1/2-1/0-(2/3-2/1)×3; and
   a third bar pattern chain of 0/0-1/1.

4. The method of claim 3 wherein there are 26 courses per inch in the mesh knit fabric.

5. The method of claim 3 wherein the mesh knit fabric is made using a 14 gauge knitting machine.

6. The method of claim 1 wherein the predetermined time is between 5 and 10 minutes.

7. The method of claim 1 wherein the predetermined temperature is between 290° F. and 310° F.

8. The method of claim 1 wherein the first pore perimeter is 20 mm.

9. A system for forming a stabilized pore within a mesh fabric comprising:
   a mesh fabric having at least one pore, said pore having a pore perimeter;
   a frame having pins for receiving the mesh fabric; and
   a support having an outer perimeter and a tapered section, the support being received into the pore so that the pore perimeter is in contact with the outer perimeter of the support, whereby, when the mesh fabric is taut within the pins of the frame and is heat set for a predetermined time at a predetermined temperature, the first pore assumes the dimension of the outer support perimeter.

10. The system of claim 9 wherein the mesh fabric is a knit fabric.

11. The system of claim 10 wherein the knit pattern is as follows:
   a first bar pattern chain of 1/0-2/3-2/1-2/3-2/1-2/3-(1/0-1/2)×3;
   a second bar pattern chain of 2/3-1/0-1/2-1/0-1/2-1/0-(2/3-2/1)×3; and
   a third bar pattern chain of 0/0-1/1.

12. The system of claim 9 wherein the fabric is made of polypropylene.

13. The system of claim 9 wherein the predetermined time is between 5 and 10 minutes.

14. The system of claim 9 wherein the predetermined temperature is between 290° F. and 310° F.

15. The system of claim 9 wherein the perimeter of the first pore is 20 mm.

16. The method of claim 1, wherein the support further comprises a tapered portion having a diameter which is smaller than a diameter corresponding to the outer perimeter of the support.

17. The system of claim 9, wherein the support further comprises a tapered portion having a diameter which is smaller than a diameter corresponding to the outer perimeter of the support.

18. A method of stabilizing a pore within a mesh fabric comprising the steps of:
   providing a mesh knit fabric made of a plurality of thermoplastic polymer yarns, the mesh fabric having a first pore, the first pore having a first perimeter;
   providing a support having an outer perimeter comprising a shape and having a tapered section;
   inserting the support into the first pore of the mesh fabric so that the first pore perimeter is in contact with the outer perimeter of the support; and
   placing the fabric and the support in an oven for a predetermined time at a predetermined temperature, whereby the first pore perimeter assumes the shape of the outer perimeter of the support.

* * * * *